(12) United States Patent
Lee et al.

(10) Patent No.: US 11,633,409 B2
(45) Date of Patent: Apr. 25, 2023

(54) SOLID PREPARATION COMPRISING DUTASTERIDE AND METHOD FOR PREPARING SAME

(71) Applicant: JW PHARMACEUTICAL CORPORATION, Seoul (KR)

(72) Inventors: Suk Lee, Seoul (KR); Min-Uk Cha, Gyeonggi-do (KR); Won-Kyu Yang, Gyeonggi-do (KR); Min-Seok Choi, Gyeonggi-do (KR)

(73) Assignee: JW PHARMACEUTICAL CORPORATION, Seoul (KR)

( * ) Notice: Subject to any disclaimer, the term of this patent is extended or adjusted under 35 U.S.C. 154(b) by 206 days.

(21) Appl. No.: 16/642,507

(22) PCT Filed: Aug. 30, 2018

(86) PCT No.: PCT/KR2018/010091
§ 371 (c)(1),
(2) Date: Feb. 27, 2020

(87) PCT Pub. No.: WO2019/045501
PCT Pub. Date: Mar. 7, 2019

(65) Prior Publication Data
US 2020/0215081 A1 Jul. 9, 2020

(30) Foreign Application Priority Data

Sep. 1, 2017 (KR) .................. 10-2017-0111953

(51) Int. Cl.
*A61K 31/58* (2006.01)
*A61K 9/107* (2006.01)
(Continued)

(52) U.S. Cl.
CPC .............. *A61K 31/58* (2013.01); *A61K 9/107* (2013.01); *A61K 9/28* (2013.01); *A61K 47/08* (2013.01)

(58) Field of Classification Search
CPC .... A61K 2300/00; A61K 31/12; A61K 31/58; A61K 45/06; A61K 31/496; A61K 31/122; A61K 31/194; A61K 31/327; A61K 31/355; A61K 31/375; A61K 31/4164; A61K 36/00; A61K 38/1816; A61K 31/18; A61K 31/337; A61K 31/192; A61K 31/473; A61K 31/4725; A61K 31/506; A61K 31/5377; A61K 9/2095; A61K 9/4808; A61K 31/4439; A61K 31/4545; A61K 31/517; A61K 9/006; A61K 31/352; A61K 36/185; A61K 47/6923; A61K 9/2072; A61K 31/05; A61K 31/095; A61K 31/155; A61K 31/167; A61K 31/465; A61K 31/7068; A61K 9/0053; A61K 9/0056; A61K 9/146; A61K 9/4858; A61K 31/616; A61K 38/063; A61K 47/6933; A61K 49/0002; A61K 49/0093; A61K 51/1251; A61K 9/48; A61K 9/4816; A61K 9/4891; A61K 9/5026; A61K 31/20; A61K 31/4709; A61K 31/4985; A61K 31/568; A61K 31/7088; A61K 31/7105; A61K 31/715; A61K 36/81; A61K 38/00; A61K 47/32; A61K 47/38; A61K 9/0024; A61K 9/0034; A61K 9/145; A61K 9/4866; A61K 31/451; A61K 36/324; A61K 36/752; A61K 47/02; A61K 47/14; A61K 9/1075; A61K 9/16; A61K 9/1652; A61K 9/2806; A61K 9/2866; A61K 9/4825; A61K 9/7007; A61K 31/135; A61K 31/166; A61K 31/282; A61K 31/285; A61K 31/417; A61K 31/4523; A61K 31/505; A61K 31/522; A61K 31/53; A61K 31/551; A61K 31/63; A61K 31/7034; A61K 31/704; A61K 31/7076; A61K 39/00; A61K 47/26; A61K 47/34; A61K 9/107; A61K 9/143; A61K 9/1611; A61K 9/1694; A61K 9/2009; A61K 9/2031; A61K 9/2081; A61K 9/2813; A61K 9/2853;
(Continued)

(56) References Cited

U.S. PATENT DOCUMENTS 5,565,467 A   10/1996 Batchelor et al.
11,219,591 B2  1/2022 Kang
(Continued)

FOREIGN PATENT DOCUMENTS

EP   2468262 A1    6/2012
KR   10-1055412 B1 8/2011
WO   2006099121 A2 9/2006

OTHER PUBLICATIONS

Kim et al. "Preparation and in Vivo Evaluation of a Dutasteride-Loaded Solid-Supersaturatable Self-Microemulsifying Drug Delivery System", Int. J. Mol. Sci. 2015, 16, 10821-10833; doi: 10.3390/ijms 160510821. (Year: 2015).*
(Continued)

*Primary Examiner* — Audrea B Coniglio
(74) *Attorney, Agent, or Firm* — Venable LLP (57) ABSTRACT

The present invention provides a solid preparation comprising, based on 100 parts by weight of the solid preparation, a self-emulsifying composition comprising 0.1 to 0.5 parts by weight of dutasteride, 6 to 110 parts by weight of oil and 6 to 110 parts by weight of a surfactant, and 5 to 185 parts by weight of a coating excipient having pores accommodating the self-emulsifying composition formed in a surface thereof, and a method of manufacturing the solid preparation.

12 Claims, 4 Drawing Sheets

(51) Int. Cl.
*A61K 9/28* (2006.01)
*A61K 47/08* (2006.01)

(58) Field of Classification Search
CPC .... A61K 9/4833; A61K 9/501; A61K 9/5015;
A61K 9/5042; A61K 9/5047; A61K
9/5073; A61K 9/7015; A61K 2236/00;
A61K 31/137; A61K 31/145; A61K
31/5517; A61K 31/722; A61K 47/08;
A61K 47/10; A61K 47/585; A61K 47/60;
A61K 47/61; A61K 47/6953; A61K
9/0043; A61K 9/08; A61K 9/10; A61K
9/1605; A61K 9/1635; A61K 9/167;
A61K 9/1682; A61K 9/209; A61K 9/28;
A61K 9/282; A61K 9/50; A61K 9/5021;
A61K 9/5078; A61K 9/5084; A61K
36/27; A61K 36/284; A61K 36/288;
A61K 36/815; A61K 36/488; A61K
36/605; A61K 36/898; A61K 36/904;
A61K 36/14; A61K 2236/15; A61K
2236/17; A61K 236/331; A61K 2236/333;
A61K 2236/37; A61K 2236/51; A61K
2236/53; A61K 36/15; A61K 8/342;
A61K 8/365; A61K 8/368; A61K 8/41;
A61K 8/44; A61K 8/9767; A61K
2800/33; A61K 31/025; A61K 31/435;
A61K 47/12; A61K 9/0014; A61K 9/06;
A61K 9/14; A61K 9/2077; A61K 35/761;
A61K 47/183; A61K 47/20; A61K
9/0019; A61K 47/44; A61K 9/1617;
A61K 9/2013; A61K 9/2022; A61K
9/2833; A61K 9/1641; A61K 9/2018;
A61K 9/2027; A61K 9/2054; A61K
9/2059; A61K 31/56; A61K 9/5057;
A61K 47/00; A61K 9/2893; A61K 9/20;
A61P 43/00; A61P 35/00; A61P 29/00;
A61P 13/08; A61P 35/02; A61P 9/12;
A61P 17/02; A61P 9/00; A61P 11/02;
A61P 25/00; A61P 3/02; A61P 3/06;
A61P 17/14; A61P 25/22; A61P 25/34;
A61P 35/04; A61P 3/00; A61P 9/10;
A61P 11/00; A61P 13/12; A61P 1/16;
A61P 25/28; A61P 31/04; A61P 17/06;
A61P 19/02; A61P 1/14; A61P 25/18;
A61P 25/30; A61P 25/36; A61P 27/02;
A61P 33/02; A61P 3/10; A61J 3/10; A61J
3/07; A61J 3/071; A61J 3/074; A61J
3/077; C08K 5/13; C08K 5/01; C08K
5/005

See application file for complete search history.

(56) References Cited

U.S. PATENT DOCUMENTS

| 11,235,015 | B2 | 2/2022 | Jia |
| 11,242,442 | B2 | 2/2022 | Roh et al. |
| 11,261,563 | B2 | 3/2022 | Joung et al. |
| 2009/0069364 | A1 | 3/2009 | Carrara et al. |
| 2015/0366805 | A1* | 12/2015 | Monsuur ............ B01J 20/28004 |
| | | | 424/489 |
| 2019/0264381 | A1 | 8/2019 | Joung et al. |
| 2020/0115525 | A1 | 4/2020 | Roh et al. |
| 2020/0164015 | A1 | 5/2020 | Jia |
| 2020/0315948 | A1 | 10/2020 | Kang |

OTHER PUBLICATIONS

Kim, Min-Soo et al., "Preparation and in Vivo Evaluation of a Dutasteride-Loaded Solid-Supersaturatable Self-Microemulsifying Drug Deliver System", International Journal of Molecular Sciences (2015), vol. 16, pp. 10821-10833.

Subramanian, P. et al., "Self-Nanoemulsifying Drug Delivery systems of Poorly Soluble Drug Dutasteride: Formulation and In-Vitro Characterization", Journal of Applied Pharmaceutical Science (2017) (Online publication date: Apr. 30, 2017), vol. 7, pp. 011-022.

Lei, Y. et al., "Solid Self-Nanoemulsifying Cyclosporin A Pelletts Prepared by Fluid-Bed Coating: Preparation, Characterization and in vitro Redispersibility", International Journal of Nanomedicine (2011), vol. 6, pp. 795-805.

Hentzchel, C.M. et al. "Suitability of Various Excipients as Carrier and Coating Materials for Liquisolid Compacts", Drug Development and Industrial Pharmacy, 2011, vol. 37, No. 10, pp. 1200-1207.

Shahba, A. Abdul-Wahhab et al., "Solidification of Cinnarizine Self-Nanoemulsifying Drug Delivery Systems by Fluid Bed Coating: Optimization of the Process and Formulation Variables", Die Pharmazie—An International Journal of Pharmaceutical Sciences, Mar. 2017, vol. 72, No. 3, pp. 143-151.

Jadhav, N.R et al., "Solid State Behavior of Progesterone and Its Release from Neusilin US2 Based Liquisolid Compacts", Journal of Drug Delivery Science and Technology, 2017 (Online publication date: Feb. 12, 2017), vol. 38, pp. 97-106.

Gumaste, S.G., et al., "Development of solid SEDDS, VI: Effect of precoating of Neusilin® US2 with PVP on drug release from adsorbed self-emulsifying lipid-based formulations," European Journal of Pharmaceutical Sciences, vol. 110, pp. 124-133 (2017).

* cited by examiner

SOLID PREPARATION COMPRISING DUTASTERIDE AND METHOD FOR PREPARING SAME

The present application is a national-stage entry under 35 U.S.C. § 371 of International Patent Application No. PCT/KR2018/010091, published as WO 2019/045501, filed Aug. 30, 2018, which claims priority to Korean Patent Application No. 10-2017-0111953, filed Sep. 1, 2017, the entire disclosure of each of which is incorporated by reference herein.

TECHNICAL FIELD

The present invention relates to a solid preparation comprising dutasteride and a method of manufacturing the same.

BACKGROUND ART

Dutasteride is known to be useful for treating benign prostatic hyperplasia and male alopecia, and has the structure of Chemical Formula 1 below, as disclosed in U.S. Pat. No. 5,565,467.

Chemical Formula 1

U.S. Patent Application Publication No. 2009/0069364 discloses that the equilibrium solubility of dutasteride is 3.06 g/100 g in isopropanol, 2.75 g/100 g in Capmul MCM NF, 2.41 g/100 g in Transcutol, 1.34 g/100 g in propylene glycol, 0.39 g/100 g in PEG 400, and 4.40 g/100 g in ethanol, and International Publication No. WO2006-099121 discloses that dutasteride is insoluble in water. Simply put, dutasteride is widely known as a very poorly soluble drug.

Dutasteride is currently commercially available as a soft capsule product under the brand name AVODART®, and AVODART is a product configured such that 0.5 mg of dutasteride is dissolved in 349.5 mg of a mixture of mono- and di-glyceride oil of caprylic/capric acid and butylated hydroxytoluene (BHT) and is loaded in a soft capsule, and is used as a therapeutic agent for the treatment of benign prostatic hyperplasia or alopecia areata.

However, since the soft capsule product is in the form of a liquid drug contained in a soft gelatin capsule, it easily softens at high temperatures, and moreover, dissolution thereof is delayed due to curing of gelatin and oil at low temperatures, and a separate production facility is required in order to manufacture and load a chemical composition in the soft capsule, undesirably incurring very high manufacturing costs. Furthermore, since capsules may break down during manufacture, storage and delivery due to the characteristics of soft capsule products, there is a need for preparations capable of overcoming the above problems.

Hence, many researchers are working on solid preparations, especially tablets, which show pharmacokinetic parameters and bioavailability equivalent to or greater than the AVODART soft capsule product, and considering that the solubility or dissolution rate of the drug is a very important factor in determining the absorption and bioavailability of the drug, various solubilization methods have been attempted in order to increase the solubility of solid particles comprising dutasteride. In particular, many studies have been conducted with the goal of manufacturing solid particles by adsorbing a self-emulsifying composition, prepared by dissolving dutasteride in oil and adding a surfactant and the like, to a predetermined excipient (adsorbent). However, when tablets are made using the solid particles manufactured by the above method, clinical trials showed problems of bioavailability lower than the AVODART soft capsule product and pharmacokinetic parameters different therefrom.

As a result of repeated research to overcome the above problems, the present inventors have developed solid particles, which have significantly improved solubility compared to the chemical composition in the AVODART soft capsule and in which dutasteride may be homogeneously distributed, and thus have ascertained the development of solid preparations exhibiting a dissolution rate and bioavailability equivalent to or greater than the AVODART soft capsule product, thereby culminating in the present invention.

(Patent Document 1) U.S. Pat. No. 5,565,467
(Patent Document 2) U.S. Patent Application Publication No. 2009/0069364
(Patent Document 3) International Publication No. WO2006-099121

DISCLOSURE

Technical Problem

An objective of the present invention is to provide solid particles, which have very high solubility compared to the chemical composition in the soft capsule of AVODART and in which dutasteride may be homogeneously distributed.

Another objective of the present invention is to provide a solid preparation such as a tablet, which exhibits pharmacokinetic parameters and bioavailability equivalent to or greater than AVODART, using the solid particles of the present invention.

Technical Solution

In order to accomplish the above objectives, the present invention provides a solid preparation, comprising, based on 100 parts by weight of the solid preparation:

a self-emulsifying composition comprising 0.1 parts by weight to 0.5 parts by weight of dutasteride, 6 parts by weight to 110 parts by weight of oil and 6 parts by weight to 110 parts by weight of a surfactant, and 5 parts by weight to 185 parts by weight of a coating excipient having pores accommodating the self-emulsifying composition formed in a surface thereof.

In addition, the present invention provides a method of manufacturing a solid preparation, comprising: manufacturing a self-emulsifying composition by mixing dutasteride, oil and a surfactant;

obtaining a coating excipient having pores accommodating the self-emulsifying composition formed in a surface thereof by coating a porous excipient, having pores accommodating the self-emulsifying composition formed in a surface thereof, with a coating agent; and manufacturing solid particles in which the self-emulsifying composition is accommodated in the pores in the coating excipient having pores accommodating the self-emulsifying composition formed in the surface thereof by mixing the self-emulsifying composition and the coating excipient having pores accommodating the self-emulsifying composition formed in the surface thereof.

Advantageous Effects

According to the present invention, the solid preparation comprises, based on 100 parts by weight of the solid preparation, a self-emulsifying composition comprising 0.1 parts by weight to 0.5 parts by weight of dutasteride, 6 parts by weight to 110 parts by weight of oil and 6 parts by weight to 110 parts by weight of a surfactant, and 5 parts by weight to 185 parts by weight of a coating excipient having pores accommodating the self-emulsifying composition formed in a surface thereof. Here, a coating agent functions to form a coating film on the surface of a porous excipient, and the coating film controls the depth of pores in the surface of the porous excipient, making the fine surface homogeneous, and blocks pores having narrow entrances or very small pores among the pores in the surface of the porous excipient, thereby preventing cases in which the self-emulsifying composition introduced into the pores having narrow entrances or very small pores is not released from the pores or in which the release thereof is delayed. A water-soluble polymer dissolves rapidly in body fluids, helping the self-emulsifying composition to produce emulsions quickly. Accordingly, when the dutasteride solid preparation enters the body's aqueous solution environment after the solid preparation comprising dutasteride is taken, the coating agent on the surface of the coating excipient having pores accommodating the self-emulsifying composition formed in the surface thereof is dissolved, and thus the self-emulsifying composition accommodated in the pores in the coating excipient can be easily released from the pores, ultimately realizing a high dissolution rate. Moreover, the solid preparation is uniformly and rapidly released and thus can exhibit a high dissolution rate and high bioavailability, making it applicable to a formulation such as a tablet or a hard capsule.

BEST MODE

The present invention pertains to a solid preparation, comprising, based on 100 parts by weight of the solid preparation, a self-emulsifying composition comprising 0.1 parts by weight to 0.5 parts by weight of dutasteride, 6 parts by weight to 110 parts by weight of oil, and 6 parts by weight to 110 parts by weight of a surfactant, and 5 parts by weight to 185 parts by weight of a coating excipient having pores accommodating the self-emulsifying composition formed in the surface thereof.

In an embodiment of the present invention, the solid preparation may comprise a self-emulsifying composition comprising 0.1 to 0.5 mg of dutasteride, 6 mg to 110 mg of oil and 6 mg to 110 mg of a surfactant, and 5 mg to 185 mg of a coating excipient having pores accommodating the self-emulsifying composition formed in the surface thereof, and preferably comprises a self-emulsifying composition comprising 0.5 mg of dutasteride, 30 mg to 110 mg of oil and 30 mg to 110 mg of a surfactant, and 25 mg to 185 mg of a coating excipient having pores accommodating the self-emulsifying composition formed in the surface thereof. More preferably, the solid preparation comprises a self-emulsifying composition comprising 0.5 mg of dutasteride, 30 mg to 75 mg of oil and 30 mg to 75 mg of a surfactant, and 93.5 mg to 123.5 mg of a coating excipient having pores accommodating the self-emulsifying composition formed in the surface thereof.

In the present invention, the coating excipient is configured such that the surface of a porous excipient is coated with a coating agent. The coating excipient having pores accommodating the self-emulsifying composition formed in the surface thereof is obtained by coating the porous excipient having pores accommodating the self-emulsifying composition formed in the surface thereof with the coating agent. For example, the coating excipient may be formed in a manner in which the porous excipient is mixed with a coating solution, obtained by mixing an organic solvent and a coating agent, and then dried.

In the present invention, the self-emulsifying composition may further comprise at least one water-soluble polymer selected from among polyethylene glycol, carboxymethyl cellulose, hydroxypropyl methyl cellulose, hydroxypropyl cellulose, polyvinylpyrrolidone, polyvinyl alcohol and polyvinyl-alcohol/polyethylene-glycol grafted copolymer. The water-soluble polymer is preferably at least one selected from among hydroxypropyl methyl cellulose, polyvinyl-alcohol/polyethylene-glycol grafted copolymer and polyvinylpyrrolidone, more preferably at least one of polyvinylpyrrolidone and hydroxypropyl methyl cellulose, and most preferably polyvinylpyrrolidone.

In the present invention, the self-emulsifying composition may be a self-emulsifying emulsion composition of dutasteride having an average emulsion particle size of 15 to 180 nm and a size distribution of 15 to 250 nm when dispersed in an aqueous phase.

The oil, which is a solubilizer for dissolving dutasteride, may be at least one selected from among glyceryl caprylate/caprate, glycerol tricaprylate/caprate, glyceryl tricaprylate/tricaprate, propylene glycol monocaprylate, propylene glycol dicaprylate/dicaprate, propylene glycol monolaurate and glyceryl monooleate, and is preferably at least one selected from among glyceryl caprylate/caprate, glycerol tricaprylate/caprate and propylene glycol monocaprylate.

The surfactant functions to stably emulsify the oil component in water to form a stable emulsion, and the surfactant may be at least one selected from among polyoxyl castor oil and derivatives thereof, polyoxyethylene-polyoxypropylene block copolymer, Tweens, Macrogol 15 hydroxystearate and sodium dodecyl sulfate, and is preferably polyoxyl castor oil and derivatives thereof, and more preferably polyoxyl 35 castor oil.

In the present invention, the porous excipient may be at least one selected from among magnesium aluminosilicate, calcium silicate, magnesium light anhydrous silicate, cellulose powder, microcrystalline cellulose, talc, silicon dioxide, lactose and calcium phosphate, and is preferably at least one of magnesium aluminosilicate and calcium silicate, and more preferably magnesium aluminosilicate.

In the present invention, the self-emulsifying composition may have an average emulsion particle size of 15 to 180 nm and a size distribution of 15 to 250 nm when dispersed in an aqueous phase, and preferably, the self-emulsifying composition has an average emulsion particle size of 15 to 100 nm and a size distribution of 15 to 150 nm when dispersed in an aqueous phase.

In the present invention, the solid preparation may further comprise at least one stabilizer selected from among butylated hydroxyanisole, butylated hydroxytoluene and dibutyl hydroxytoluene, in order to inhibit oxidation and hydrolysis.

In the present invention, the solid preparation may be provided in the form of a formulation, such as a tablet, a hard capsule, a compression-coated tablet, a bilayer tablet or a triple-layer tablet, and is preferably a tablet.

In the present invention, the coating agent may be at least one selected from among polyethylene glycol, carboxymethyl cellulose, hydroxypropyl methyl cellulose, hydroxypropyl cellulose, polyvinylpyrrolidone, polyvinyl alcohol and polyvinyl-alcohol/polyethylene-glycol grafted copolymer, and is preferably at least one selected from among hydroxypropyl methyl cellulose, polyvinyl-alcohol/polyethylene-glycol grafted copolymer and polyvinylpyrrolidone, more preferably at least one of polyvinylpyrrolidone and hydroxypropyl methyl cellulose, and most preferably polyvinylpyrrolidone.

The coating agent is responsible for forming a coating film on the surface of the porous excipient, and the coating film controls the depth of pores in the surface of the porous excipient and blocks pores having a very small diameter, thus facilitating the movement of the self-emulsifying composition into and out of the pores.

In an embodiment of the present invention, the solid preparation may comprise 0.1 to 0.5 mg of dutasteride, taking into consideration a known typical daily dose.

In an embodiment of the present invention, the solid preparation is preferably orally administered.

The present invention pertains to a method of manufacturing a solid preparation, comprising manufacturing a self-emulsifying composition by mixing dutasteride, oil and a surfactant;

obtaining a coating excipient having pores accommodating the self-emulsifying composition formed in a surface thereof by coating a porous excipient, having pores accommodating the self-emulsifying composition formed in a surface thereof, with a coating agent; and manufacturing solid particles in which the self-emulsifying composition is accommodated in the pores in the coating excipient having pores accommodating the self-emulsifying composition formed in the surface thereof by mixing the self-emulsifying composition and the coating excipient having pores accommodating the self-emulsifying composition formed in the surface thereof.

In the present invention, the oil may be at least one selected from among glyceryl caprylate/caprate, glycerol tricaprylate/caprate, glyceryl tricaprylate/tricaprate, propylene glycol monocaprylate, propylene glycol dicaprylate/dicaprate, propylene glycol monolaurate and glyceryl monooleate, and is preferably at least one selected from among glyceryl caprylate/caprate, glycerol tricaprylate/caprate and propylene glycol monocaprylate.

In the present invention, the surfactant may be at least one selected from among polyoxyl castor oil and derivatives thereof, polyoxyethylene-polyoxypropylene block copolymer, Tweens, Macrogol 15 hydroxystearate and sodium dodecyl sulfate, and is preferably polyoxyl castor oil and derivatives thereof, and more preferably polyoxyl 35 castor oil.

In the present invention, the coating agent may be at least one selected from among polyethylene glycol, carboxymethyl cellulose, hydroxypropyl methyl cellulose, hydroxypropyl cellulose, polyvinylpyrrolidone, polyvinyl alcohol and polyvinyl-alcohol/polyethylene-glycol grafted copolymer, and is preferably at least one selected from among hydroxypropyl methyl cellulose, polyvinyl-alcohol/polyethylene-glycol grafted copolymer and polyvinylpyrrolidone, more preferably at least one of polyvinylpyrrolidone and hydroxypropyl methyl cellulose, and most preferably polyvinylpyrrolidone.

The coating agent is responsible for forming a coating film on the surface of the porous excipient, and the coating film controls the depth of pores in the surface of the porous excipient and blocks pores having a very small diameter, thus facilitating the movement of the self-emulsifying composition into and out of the pores.

The amount of the porous excipient may be 4 to 130 parts by weight. When the amount of the porous excipient falls in the above range, the amount of the coating agent may be 1 to 55 parts by weight.

In a preferred embodiment, the amount of the porous excipient is preferably 4 to 130 mg. When the amount of the porous excipient is 4 to 130 mg, the amount of the coating agent is preferably 1 to 55 mg. In particular, if the amount of the coating agent exceeds 55 mg, pores having a diameter that facilitates movement of the self-emulsifying composition into and out of the pores may also be excessively blocked.

In the present invention, the water-soluble polymer may be at least one selected from among polyethylene glycol, carboxymethyl cellulose, hydroxypropyl methyl cellulose, hydroxypropyl cellulose, polyvinylpyrrolidone, polyvinyl alcohol and polyvinyl-alcohol/polyethylene-glycol grafted copolymer, and is preferably at least one selected from among hydroxypropyl methyl cellulose, polyvinyl-alcohol/polyethylene-glycol grafted copolymer and polyvinylpyrrolidone, more preferably at least one of polyvinylpyrrolidone and hydroxypropyl methyl cellulose, and most preferably polyvinylpyrrolidone. Due to the coating agent and the water-soluble polymer, rapid and homogeneous drug release in body fluids and high dissolution rate and bioavailability are achieved.

In the present invention, the manufacturing the self-emulsifying composition by mixing the dutasteride, the oil and the surfactant may comprise stirring and mixing at least one oil selected from among glyceryl caprylate/caprate, glycerol tricaprylate/caprate, glyceryl tricaprylate/tricaprate, propylene glycol monocaprylate, propylene glycol dicaprylate/dicaprate, propylene glycol monolaurate and glyceryl monooleate;

adding the stirred oil with dutasteride, followed by mixing and complete dissolution; and adding the stirred oil in which the dutasteride is completely dissolved with at least one surfactant selected from among polyoxyl castor oil and derivatives thereof, polyoxyethylene-polyoxypropylene block copolymer, Tweens, Macrogol 15 hydroxystearate and sodium dodecyl sulfate, followed by re-stirring and mixing.

In the present invention, during the adding the stirred oil with dutasteride, followed by mixing and complete dissolution, the stirred oil may be further added with a stabilizer selected from among butylated hydroxyanisole, butylated hydroxytoluene and dibutyl hydroxytoluene, and may thus be completely dissolved.

Mode for Invention

A better understanding of the present invention will be given through the following examples.

EXAMPLES

The present invention is specified below, but the present invention is not limited to the following examples.

Example 1. Manufacture of Coating Excipient Having Pores Accommodating Self-Emulsifying Composition Formed in Surface Thereof A commercially available porous excipient was coated with a water-soluble polymer comprising components in the amounts shown in Table 1 below (hereinafter referred to as a "coating agent"), thereby manufacturing the coating excipient of each of Example 1-1 and Example 1-2, having pores accommodating a self-emulsifying composition formed in the surface thereof.

Specifically, as a coating agent, a water-soluble polymer polyvinylpyrrolidone (PVP K-25) was added and mixed in a vessel containing anhydrous ethanol to afford a coating solution. As a porous excipient having pores formed in the surface thereof, magnesium aluminometasilicate (Neusilin US2) was mixed with the coating solution using a high-speed mixer, and the resulting mixture was dried at about 60° C., thus obtaining a coating excipient having pores accommodating a self-emulsifying composition formed in the surface thereof. In the coating excipient having pores accommodating the self-emulsifying composition formed in the surface thereof, the entrances of pores having a very small diameter among pores in the surface of the porous excipient are blocked with the coating agent, or the insides of the pores are filled therewith, and pores having a diameter that facilitates the movement of the self-emulsifying composition particles into and out of the pores are maintained in the state in which the inner surface thereof is coated. Here, the pores having a very small diameter have an entrance diameter or inner diameter similar to or smaller than the self-emulsifying composition comprising dutasteride, and indicate pores having an entrance diameter or inner diameter that does not facilitate the movement of the self-emulsifying composition into and out of the pores. This prevents the late release or non-release of the self-emulsifying composition comprising dutasteride by being trapped in the pores in the porous excipient in the body of a patient taking the solid preparation according to the present invention.

Here, calcium silicate, magnesium light anhydrous silicate, cellulose powder, microcrystalline cellulose, talc, silicon dioxide, lactose and calcium phosphate may be used as the porous excipient in lieu of magnesium aluminometasilicate, and as the coating agent, at least one selected from among hydroxypropyl methyl cellulose, polyvinyl-alcohol/polyethylene-glycol grafted copolymer and polyvinylpyrrolidone may be used. The amount of the porous excipient is preferably 20 to 130 mg and the amount of the coating agent is preferably 5 to 55 mg. In particular, if the amount of the coating agent exceeds 55 mg, pores having a diameter that facilitates the movement of the self-emulsifying composition into and out of the pores may also be excessively blocked.

Example 2. Manufacture of Solid Particles Comprising Dutasteride

Solid particles containing dutasteride were manufactured using components in the amounts shown in Table 2 below.

Specifically, as oil, glyceryl caprylate/caprate (Capmul MCM NF) and glycerol tricaprylate/caprate (Captex 355) were placed in a vessel, stirred and mixed well; after a predetermined time, the stirred oil was added with dutasteride and butylated hydroxytoluene as a stabilizer, mixed, and completely dissolved; and the stirred oil in which dutasteride was completely dissolved was added with polyoxyl 35 castor oil (Kolliphor EL) as a surfactant and re-stirred to afford an oil solution. Polyvinylpyrrolidone (PVP K-25) as a water-soluble polymer was placed in a vessel containing anhydrous ethanol and mixed to afford a homogenous solution, which was then mixed with the oil solution, thereby preparing a self-emulsifying composition. The self-emulsifying composition thus prepared has an average emulsion particle size of 15 to 180 nm and a size distribution of 15 to 250 nm when dispersed in an aqueous phase.

In the present invention, the amount of the oil and the amount of the surfactant are controlled, making it possible to achieve solid particles exhibiting a dissolution rate equivalent to or higher than the AVODART chemical composition. Additionally, in the present example, the water-soluble polymer interacts with the coating agent to facilitate the movement of the self-emulsifying composition into and out of the pores in the coating excipient and also to enable quick formation of a homogeneous emulsion in the body, resulting in rapid and homogeneous drug release and high dissolution rate and bioavailability.

The self-emulsifying composition was mixed with the coating excipient having pores accommodating the self-emulsifying composition formed in the surface thereof manufactured in Example 1-1 using a high-speed mixer, and dried at about 60° C., thus manufacturing the solid particles of Example 2-1 to Example 2-3 in which the self-emulsifying composition was accommodated in the pores in the surface of the coating excipient having pores accommodating the self-emulsifying composition formed in the surface thereof.

TABLE 1

(unit: mg)

| Component | Example 1-1 | Example 1-2 |
| --- | --- | --- |
| Coating agent (polyvinylpyrrolidone K-25) | 10 | 40 |
| Porous excipient (magnesium aluminometasilicate) | 83.5 | 83.5 |

TABLE 2

(unit: mg)

| Component | Example 2-1 | Example 2-2 | Example 2-3 |
| --- | --- | --- | --- |
| Dutasteride | 0.5 | 0.5 | 0.5 |
| Oil (glyceryl caprylate/caprate) | 15 | 25 | 37.5 |
| Oil (glycerol tricaprylate/caprate) | 15 | 25 | 37.5 |

TABLE 2-continued (unit: mg)

| Component | Example 2-1 | Example 2-2 | Example 2-3 |
|---|---|---|---|
| Surfactant (polyoxyl 35 castor oil) | 30 | 50 | 75 |
| Stabilizer (butylated hydroxytoluene) | 0.2 | 0.2 | 0.2 |
| Coating agent (polyvinylpyrrolidone K-25) | 10 | 10 | 10 |
| Water-soluble polymer (polyvinylpyrrolidone K-25) | 10 | 10 | 10 |
| Porous excipient (magnesium aluminometasilicate) | 83.5 | 83.5 | 83.5 |

Meanwhile, the present inventors have ascertained that when the amounts of surfactant and/or oil are excessive, the solid particles may agglomerate, making it difficult to ensure homogeneity of the preparation and to manufacture a solid preparation such as a tablet or a hard capsule. The preferred amount of each of the surfactant and oil was 30 mg to 110 mg based on 0.5 mg of dutasteride in order to prevent such agglomeration and to exhibit a dissolution rate of a certain level or more.

As the surfactant, not only polyoxyl castor oil but also derivatives thereof, polyoxyethylene-polyoxypropylene block copolymer, Tweens, Macrogol 15 hydroxystearate and sodium dodecyl sulfate may be used.

In addition to the oil used in Table 2, glyceryl caprylate/caprate, glycerol tricaprylate/caprate, glyceryl tricaprylate/tricaprate, propylene glycol monocaprylate, propylene glycol dicaprylate/dicaprate, propylene glycol monolaurate and glyceryl monooleate may be used.

Example 3. Manufacture of Tablet (Solid Preparation) Comprising Dutasteride Solid Particles A tablet was manufactured using the solid particles of Example 2-2 and the external excipient and lubricant shown in Table 3 below, and coated with an external coating agent.

Specifically, the solid particles and the external excipient comprising crospovidone, lactose hydrate, anhydrous calcium phosphate and microcrystalline cellulose were placed in a V-mixer and mixed. After completion of mixing, sodium stearyl fumarate as a lubricant was further added to the mixture in the V-mixer, followed by final mixing to complete the lubricating process. The resulting mixture was manufactured into a tablet using a rotary tableting machine. Here, the hardness of the tablet was 7 to 9 kp and the wear test result was less than 1%.

An external coating solution was prepared by stirring the external coating agent shown in Table 3 below in a mixed solution of anhydrous ethanol and purified water in an amount corresponding to 10 times the amount of the external coating agent. Here, the ratio of anhydrous ethanol and purified water was 8:2. The tablet was coated with the external coating solution prepared above to afford a coated tablet.

TABLE 3

(unit: mg)

| Classification | Component | Example 3 |
|---|---|---|
| Solid particles | Dutasteride | 0.5 |
| | Oil (glyceryl caprylate/caprate) | 25 |
| | Oil (glycerol tricaprylate/caprate) | 25 |
| | Surfactant (polyoxyl 35 castor oil) | 50 |
| | Coating agent (polyvinylpyrrolidone K-25) | 10 |
| | Water-soluble polymer (polyvinylpyrrolidone K-25) | 10 |
| | Stabilizer (butylated hydroxytoluene) | 0.2 |
| | Porous excipient (magnesium aluminometasilicate) | 83.5 |
| | Total of solid preparation | 204.2 |
| External excipient | Microcrystalline cellulose | 45 |
| | Lactose hydrate | 40.1 |
| | Anhydrous calcium hydrogen phosphate | 170 |
| | Crospovidone | 37.2 |
| Lubricant | Sodium stearyl fumarate | 3.5 |
| | Total of tablet | 500 |
| External coating agent | Opadry yellow | 20 |
| | Total of coated tablet | 520 |

Comparative Example 1. Solid Particles Comprising Dutasteride Containing Low or Excessive Amount of Oil and Surfactant Compared to the Present Invention The solid particles containing dutasteride of Comparative Examples 1-1 to 1-3 were manufactured using components in the amounts shown in Table 4 below. The amounts of the components, except for the oil and surfactant, and the preparation method were the same as in Example 2.

TABLE 4

(unit: mg)

| Component | Comparative Example 1-1 | Comparative Example 1-2 | Comparative Example 1-3 |
|---|---|---|---|
| Dutasteride | 0.5 | 0.5 | 0.5 |
| Oil (glyceryl caprylate/caprate) | 5 | 10 | 60 |
| Oil (glycerol tricaprylate/caprate) | 5 | 10 | 60 |
| Surfactant (polyoxyl 35 castor oil) | 10 | 20 | 120 |
| Stabilizer (butylated hydroxytoluene) | 0.2 | 0.2 | 0.2 |
| Coating agent (polyvinylpyrrolidone K-25) | 10 | 10 | 10 |
| Water-soluble polymer (polyvinylpyrrolidone K-25) | 10 | 10 | 10 |
| Porous excipient (magnesium aluminometasilicate) | 83.5 | 83.5 | 83.5 |

Comparative Example 2. AVODART

A currently commercially available soft capsule, AVODART® 0.5 mg, corresponding to 0.5 mg of dutasteride, was used as Comparative Example 2.

Experimental Example 1. Comparative Evaluation of Outer Appearance of Solid Particles of Examples 2-1 to 2-3 and Solid Particles of Comparative Example 1-3

Figure 1:
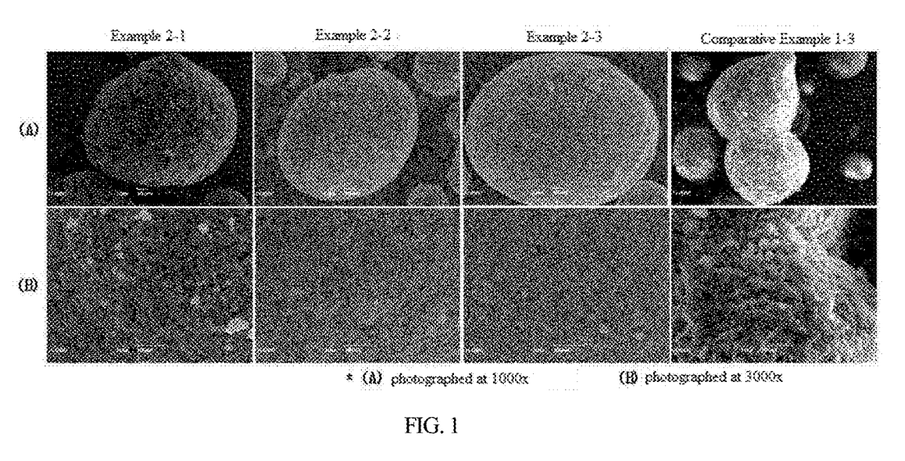
FIG. 1 shows images of the solid particles of Examples 2-1 to 2-3 according to the present invention and the solid particles of Comparative Example 1-3.

In order to evaluate the outer surface of the solid particles of Examples 2-1 to 2-3 and Comparative Example 1-3, the outer appearance thereof was observed using a scanning electron microscope at magnifications of 1000× and 3000×. The results thereof are shown in FIG. 1. As shown in FIG. 1, as the amounts of oil and surfactant increased, the pores in the surface of the coating excipient were filled and approximated spheres. In Comparative Example 1-3, when 120 mg of oil and 120 mg of surfactant were added together based on 0.5 mg of dutasteride, coating excipient agglomeration occurred, and the shape of the particles was not uniform, and moreover, it was not easy to manufacture the solid preparation due to a portion of the self-emulsifying composition not accommodated in the pores in the coating excipient.

Experimental Example 2. Average Emulsion Particle Size and Distribution of Solid Particles of Example 2

The average size and size distribution of emulsion particles formed by dispersing the solid particles of Examples 2-1 to 2-3 in 50 ml of purified water were measured using an ELS-Z particle size analyzer. The results thereof are shown in Table 5 below. As shown in Table 5, the solid particles of Examples 2-1 to 2-3 of the present invention did not differ greatly in emulsion particle size and distribution, and were homogeneous, even with changes in the amounts of oil and surfactant.

TABLE 5

| No. | | Average size and size distribution (nm) |
|---|---|---|
| Example | 2-1 | 79.3 (70.1-87.5) |
| | 2-2 | 32.8 (24.9-40.7) |
| | 2-3 | 27.8 (21.9-41.8) |

Experimental Example 3. Evaluation 1 of Dissolution Rate of Solid Particles of Examples 2-1 to 2-3 and Comparative Examples 1-1 and 1-2

The solid particles of Examples 2-1 to 2-3 and Comparative Examples 1-1 and 1-2 were subjected to a dissolution test under the following conditions.

In the dissolution evaluation of the present invention, the dissolution test was performed without the addition of a surfactant in a pH 1.2 medium resembling gastric juice conditions. In accordance with the paddle method, among the dissolution test methods described in the Korean Pharmacopoeia, the rotation speed was set to 50 rpm and the dissolution medium was sampled after 5 min, 10 min, 15 min, 30 min, 45 min, 60 min, 90 min, and 120 min and then filtered using a 0.45 μm membrane filter, and the resulting filtrate was used as a test solution. High-performance liquid chromatography was used for analysis, and the measurement wavelength was 210 nm.

Figure 2:
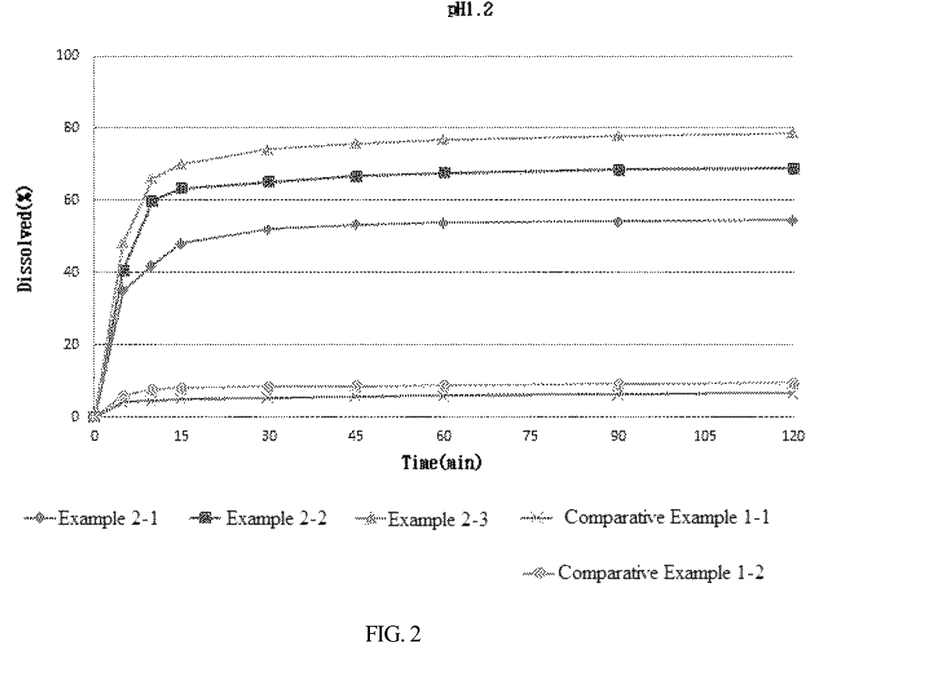
FIG. 2 is a graph showing the results of comparison of dissolution rate of the solid particles of Examples 2-1 to 2-3 according to the present invention and the solid particles of Comparative Examples 1-1 and 1-2.

The results thereof are shown in FIG. 2. As shown in FIG. 2, the solid particles of Examples 2-1 to 2-3 according to the present invention were dissolved even under the medium conditions without the surfactant, but when the amount of each of the oil and surfactant was less than 30 mg based on 0.5 mg of dutasteride, the resulting dissolution rate was lower than the dissolution rate of the solid particles of Examples 2-1 to 2-3.

Experimental Example 4. Evaluation 2 of Dissolution Rate of Solid Particles of Examples 2-1 to 2-3 and Comparative Example 1-2

The solid particles of Examples 2-1 to 2-3 and Comparative Example 1-2 were subjected to a dissolution test under the following conditions.

In order to evaluate the dissolution rate difference of the solid particles of Examples 2-1 to 2-3 and the solid particles of Comparative Example 1-2, the dissolution test was performed using 900 ml of a dissolution medium in which 2% sodium dodecyl sulfate was dissolved in 0.1 N HCl. In accordance with the paddle method, among the dissolution test methods described in the Korean Pharmacopoeia, the rotation speed was set to 50 rpm, and the dissolution medium was sampled after 5 min, 10 min, 15 min, and 30 min and then filtered using a 0.45 μm membrane filter, and the resulting filtrate was used as a test solution. High-performance liquid chromatography was used for analysis, and the measurement wavelength was 210 nm.

Figure 3:
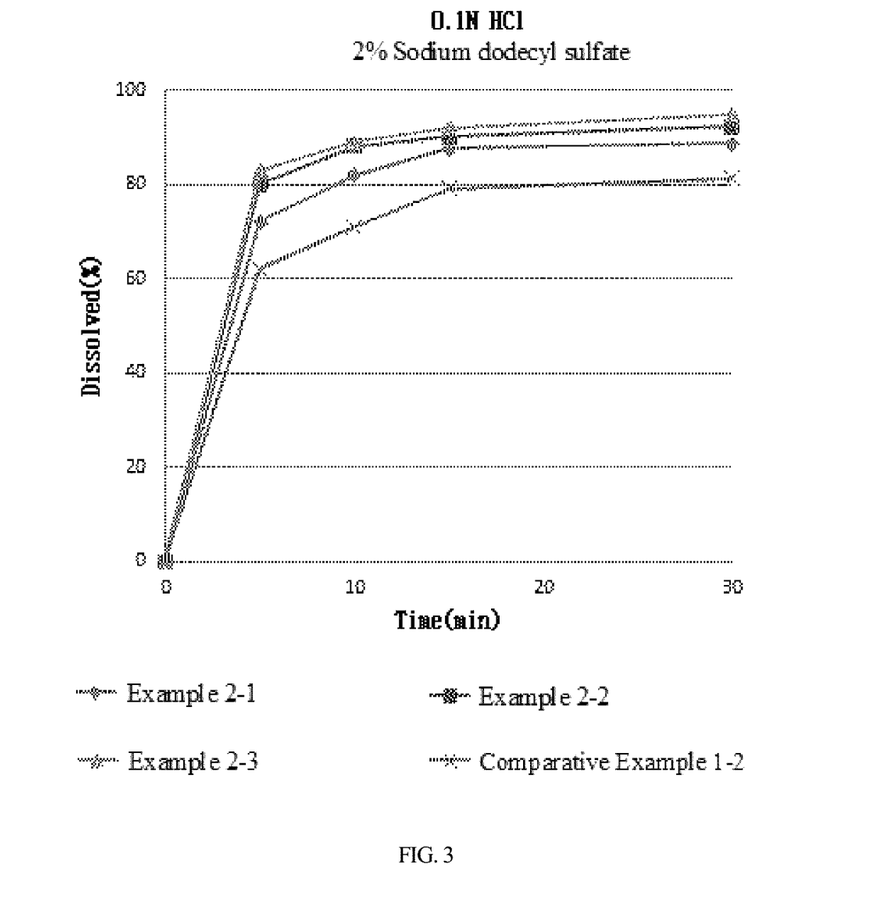
FIG. 3 is a graph showing the results of comparison of dissolution rate of the solid particles of Examples 2-1 to 2-3 according to the present invention and the solid particles of Comparative Example 1-2.

The results thereof are shown in FIG. 3 and in Table 6 below. As shown in FIG. 3 and in Table 6, the solid particles of Example 2 of the present invention exhibited a final dissolution rate of 88.6 to 94.9%, whereas the solid particles of Comparative Example 1-2, in which the amounts of oil and surfactant were lower than those of the solid particles of Examples 2-1 to 2-3, exhibited a relatively low final dissolution rate of 81.2%.

TABLE 6

| Dissolution result | Example 2-1 | Example 2-2 | Example 2-3 | Comparative Example 1-2 |
|---|---|---|---|---|
| Final dissolution rate (%) | 88.6 | 92.0 | 94.9 | 81.2 |
| Dissolution variation (%) | 1.0 | 0.9 | 1.2 | 1.4 |

Figure 4:
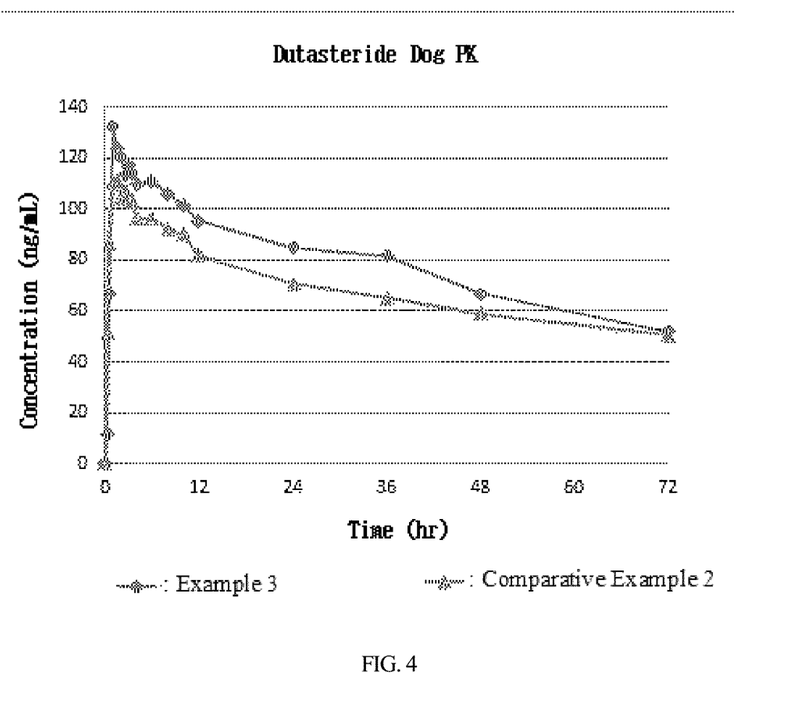
FIG. 4 is a graph showing the results of comparison of bioavailability of the tablet of Example 3 according to the present invention and the commercially available preparation of Comparative Example 2.

Experimental Example 5. Comparative Evaluation of Bioavailability of Dutasteride Upon oral administration of the tablet (solid preparation) of Example 3 and the commercially available AVODART® soft capsule of Comparative Example 2, a bioavailability comparison test was conducted on beagles. A total of 10 beagles, comprising 5 beagles per group, were used, and beagles starved for 16 hr the day before were orally administered with the tablet of Example 3 or the commercially available preparation AVODART of Comparative Example 2 such that dutasteride was administered in a dose of 0.5 mg/individual, and were then fed with 10 ml of water. 0, 0.25, 0.5, 1, 1.5, 2, 2.5, 3, 3.5, 4, 6, 8, 10, 12, 24, 36, 48 and 72 hr after oral administration, the blood was collected and analyzed to determine the pharmacokinetic parameters of dutasteride. The maximum blood concentration ($C_{max}$) and the time at maximum blood concentration ($T_{max}$) were determined directly from the blood concentration graph, and the area under the curve (AUC) of blood concentration up to 72 hr after administration was calculated based on the trapezoidal formula. The results thereof are shown in Table 6 below and in FIG. 4. As shown in Table 7 and in FIG. 4, the tablet of Example 3 exhibited pharmacokinetic parameters equivalent to or greater than the commercially available preparation of Comparative Example 2, and the variation between individuals was small.

TABLE 7

| No. | AUC | $C_{max}$ | $T_{max}$ |
|---|---|---|---|
| Example 3 | 5591.27 ± 907.31 | 143.08 ± 24.97 | 1.8 ± 0.81 |
| Comparative Example 2 (Commercially available preparation) | 4415.07 ± 2357.94 | 120.12 ± 45.85 | 1.4 ± 0.86 |

AUC: Area under the curve of blood concentration up to 72 hr after administration
$C_{max}$: Maximum blood concentration
$T_{max}$: Time at maximum blood concentration

INDUSTRIAL APPLICABILITY

According to the present invention, the solid preparation comprises, based on 100 parts by weight of the solid preparation, a self-emulsifying composition comprising 0.1 parts by weight to 0.5 parts by weight of dutasteride, 6 parts by weight to 110 parts by weight of oil and 6 parts by weight to 110 parts by weight of a surfactant, and 5 parts by weight to 185 parts by weight of a coating excipient having pores accommodating the self-emulsifying composition formed in a surface thereof. Here, a coating agent functions to form a coating film on the surface of a porous excipient, and the coating film controls the depth of pores in the surface of the porous excipient, making the fine surface homogeneous, and blocks pores having narrow entrances or very small pores among the pores in the surface of the porous excipient, thereby preventing cases in which the self-emulsifying composition introduced into the pores having narrow entrances or very small pores is not released from the pores or in which the release thereof is delayed. A water-soluble polymer dissolves rapidly in body fluids, helping the self-emulsifying composition to produce emulsions quickly. Accordingly, when the dutasteride solid preparation enters the body's aqueous solution environment after the solid preparation comprising dutasteride is taken, the coating agent on the surface of the coating excipient having pores accommodating the self-emulsifying composition formed in the surface thereof is dissolved, and thus the self-emulsifying composition accommodated in the pores in the coating excipient can be easily released from the pores, ultimately realizing a high dissolution rate. Moreover, the solid preparation is uniformly and rapidly released and thus can exhibit a high dissolution rate and high bioavailability, making it applicable to a formulation such as a tablet or a hard capsule.

The invention claimed is:

1. A solid preparation, comprising:
a self-emulsifying composition comprising 0.5 parts by weight of dutasteride; 30 to 110 parts by weight of oil; and 30 to 110 parts by weight of a surfactant, and
25 to 185 parts by weight of a coated porous excipient comprising a porous excipient and a coating agent,
wherein the porous excipient has pores accommodating the self-emulsifying composition formed in a surface thereof,
wherein the porous excipient is coated with the coating agent, in the absence of the self-emulsifying composition, by forming a mixture comprising the porous excipient and a coating solution, the coating solution comprising an organic solvent and the coating agent, then drying the mixture to form the coated porous excipient, and
wherein the coating agent is 10 to 40 parts by weight based on 83.5 parts by weight of the porous excipient, and wherein the solid preparation comprises the self-emulsifying composition in the pores of the coated porous excipient.

2. The solid preparation of claim 1, wherein the self-emulsifying composition further comprises at least one water-soluble polymer selected from among polyethylene glycol, carboxymethyl cellulose, hydroxypropyl methyl cellulose, hydroxypropyl cellulose, polyvinylpyrrolidone, polyvinyl alcohol and polyvinyl-alcohol/polyethylene-glycol grafted copolymer.

3. The solid preparation of claim 2, wherein the self-emulsifying composition is a self-emulsifying emulsion composition of dutasteride having an average emulsion particle size of 15 to 180 nm and a size distribution of 15 to 250 nm when dispersed in an aqueous phase.

4. The solid preparation of claim 1, wherein the oil is at least one selected from among glyceryl caprylate/caprate, glycerol tricaprylate/caprate, glyceryl tricaprylate/tricaprate, propylene glycol monocaprylate, propylene glycol dicaprylate/dicaprate, propylene glycol monolaurate and glyceryl monooleate.

5. The solid preparation of claim 1, wherein the surfactant is at least one selected from among polyoxyl castor oil, polyoxyethylene-polyoxypropylene block copolymer, Tweens, Macrogol 15 hydroxystearate and sodium dodecyl sulfate.

6. The solid preparation of claim 1, wherein the porous excipient is at least one selected from among magnesium aluminosilicate, calcium silicate, magnesium light anhydrous silicate, cellulose powder, microcrystalline cellulose, talc, silicon dioxide, lactose and calcium phosphate.

7. The solid preparation of claim 1, further comprising at least one stabilizer selected from among butylated hydroxyanisole, butylated hydroxytoluene and dibutyl hydroxytoluene.

8. The solid preparation of claim 1, wherein the solid preparation is a tablet.

9. The solid preparation of claim 1, wherein the coating agent is at least one selected from among polyethylene glycol, carboxymethyl cellulose, hydroxypropyl methyl cellulose, hydroxypropyl cellulose, polyvinylpyrrolidone, polyvinyl alcohol and polyvinyl-alcohol/polyethylene-glycol grafted copolymer.

10. A method of manufacturing a solid preparation, comprising:
manufacturing a self-emulsifying composition by mixing dutasteride, oil and a surfactant;
obtaining a coated porous excipient having pores for accommodating the self-emulsifying composition formed in a surface thereof by coating a porous excipient having pores, with a coating agent, in the absence of the self-emulsifying composition, by forming a mixture comprising the porous excipient and a coating solution, the coating solution comprising an organic solvent and the coating agent, then drying the mixture to form the coated porous excipient; and
manufacturing solid particles in which the self-emulsifying composition is accommodated in the pores of the coated porous excipient by mixing the self-emulsifying composition and the coated porous excipient,
wherein the self-emulsifying composition contains 0.5 parts by weight of the dutasteride, 30 to 110 parts by weight of the oil and 30 to 110 parts by weight of the surfactant,
wherein the coated porous excipient is in an amount of 25 to 185 parts by weight of the solid preparation, and wherein the coating agent is an amount of 10 to 40 parts by weight based on 83.5 parts by weight of the porous excipient.

11. The method of claim 10, wherein the porous excipient is at least one selected from among magnesium aluminosilicate, calcium silicate, magnesium light anhydrous silicate, cellulose powder, microcrystalline cellulose, talc, silicon dioxide, lactose and calcium phosphate.

12. The method of claim 10, wherein the coating agent is at least one selected from among polyethylene glycol, carboxymethyl cellulose, hydroxypropyl methyl cellulose, hydroxypropyl cellulose, polyvinylpyrrolidone, polyvinyl alcohol and polyvinyl-alcohol/polyethylene-glycol grafted copolymer.

* * * * *